United States Patent [19]
Kalb et al.

[11] Patent Number: 5,476,434
[45] Date of Patent: *Dec. 19, 1995

[54] FEMALE INCONTINENCE DEVICE INCLUDING ELECTRONIC SENSORS

[76] Inventors: Irvin M. Kalb, 327 Alta Ave., Santa Monica, Calif. 90402; Robert H. Shaw, 243 Peck Dr., Beverly Hills, Calif. 90212; Michael J. Ram, One Horseshoe Rd., Bell Canyon, Calif. 91307

[*] Notice: The term of this patent shall not extend beyond the expiration date of Pat. No. 5,352,182.

[21] Appl. No.: 284,260

[22] Filed: Aug. 2, 1994

Related U.S. Application Data

[63] Continuation-in-part of Ser. No. 888,597, May 27, 1992, Pat. No. 5,352,182.

[51] Int. Cl.⁶ ....................................................... A61F 2/02
[52] U.S. Cl. ................................ 600/30; 604/55; 604/93; 604/247; 606/193
[58] Field of Search ............................... 604/93, 96–104, 604/55, 246, 247, 329–330, 65–67; 606/191, 192, 193, 194; 600/29–31; 128/637, 903–905

[56] References Cited

U.S. PATENT DOCUMENTS

| | | | |
|---|---|---|---|
| 5,002,055 | 3/1991 | Merki et al. | 604/66 |
| 5,251,633 | 10/1993 | Wunderling | 128/637 |
| 5,271,398 | 12/1993 | Schlain et al. | 128/637 |
| 5,351,686 | 10/1994 | Steuer et al. | 128/637 |
| 5,352,182 | 10/1994 | Kalb et al. | 600/30 |
| 5,354,318 | 10/1994 | Taepke | 128/637 |

*Primary Examiner*—C. Fred Rosenbaum
*Assistant Examiner*—Chalin Smith

[57] ABSTRACT

A system for controlling drainage of the female bladder comprising a valved catheter, a stylet for placing the catheter in the female urethra, and a spike for opening the valve in the catheter to allow voiding of the contents of the bladder which also includes sensing and transmission means incorporated therein. The valve which may be integral with the shaft or located in a cap on the shaft may be manually operated or opened electronically by a signal transmitted from an external source.

12 Claims, 6 Drawing Sheets

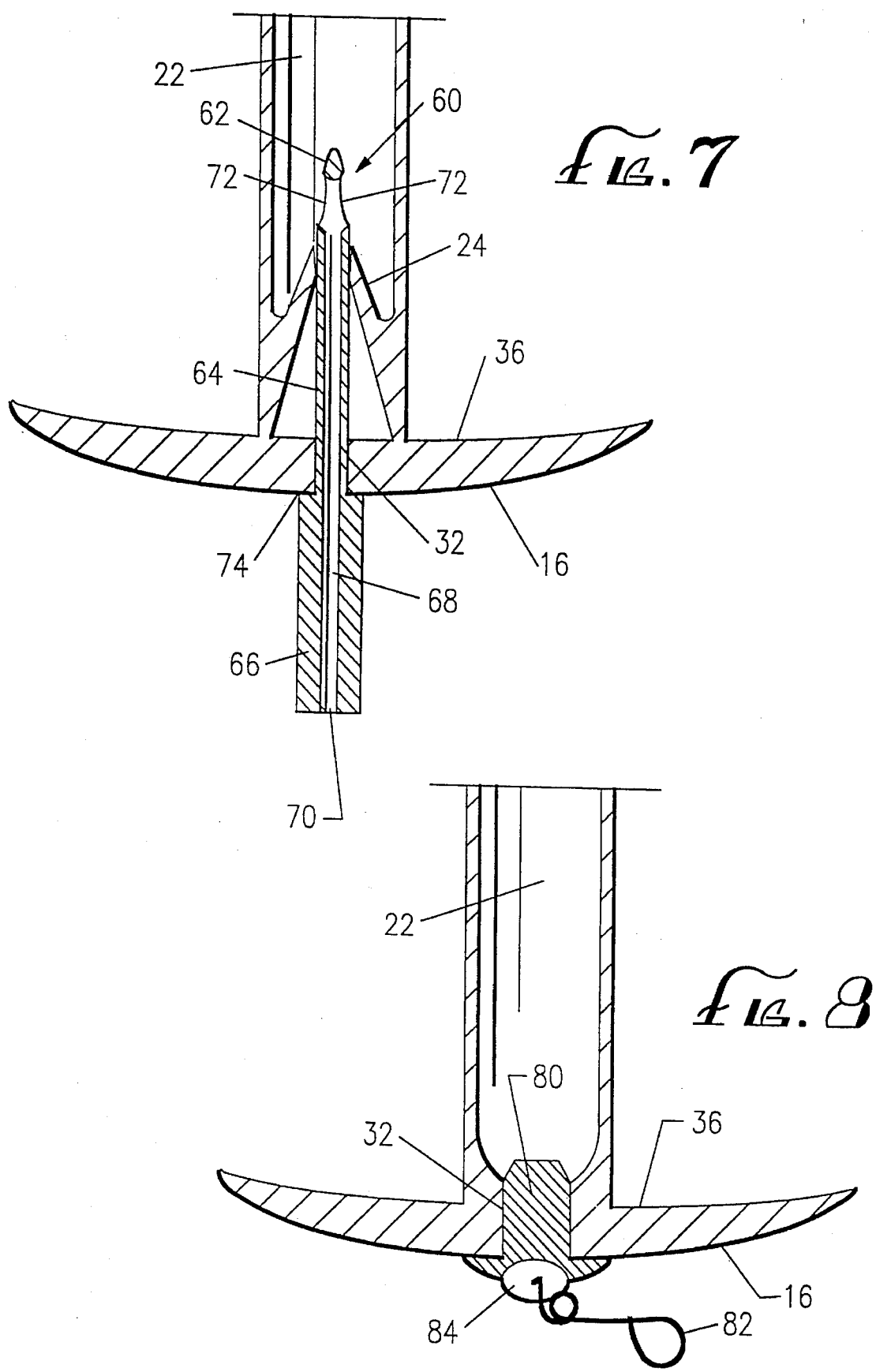

5,476,434

FEMALE INCONTINENCE DEVICE INCLUDING ELECTRONIC SENSORS

BACKGROUND

This is a continuation-in-part application of U.S. application Ser. No. 07/888,597 filed on May 27, 1992 now U.S. Pat. No. 5,352,182 issued Oct. 4, 1994. The present invention relates to a device and a method to control urination in an incontinent female and simultaneously monitor bladder pressure and urine chemistry.

A wide spread medical problem suffered by at least 11 million American adults, particularly women is incontinence. Many more suffer from the problem but, because of embarrassment or because the problem is only intermittent,, don't disclose their lack of bladder control. There are numerous causes including pregnancy, stress, as well as the normal aging process.

There presently are no adequate non-surgical techniques for treating this problem. Catheters with an attached bags are uncomfortable and are known to lead to urinary infection. Pads may be effective for small urinary leakage, such as occurs under stress, but are not suitable for large volumes of urine evacuated from a full bladder. Additionally, the use of pads requires the user to carry a large supply of replacement pads. Urethral plugs are unacceptable replacements because the user frequently will soil her hands trying to remove the device, reinsertion of the nonsterile device may lead to a bladder infection and the frequent insertion of the plug, possibly a dozen times a day, can damage the urethra and may cause bladder spasms. Plugs may also be dangerous because they totally obstruct the urethra and may result in excessive retention of urine.

A further problem which exists with certain bedridden female patients is that they may not have the ability to reach a bathroom to void and may need nursing assistance or they may not have the ability to sense when their bladder is full so that they can urinate without soiling themselves or the bed linen.

Thus there is a need for a convenient, relatively clean, and frequently repeatable procedure which can be practiced by the woman and nursing personnel and devices which can be used in the procedure. The devices must also be safe to use, discrete, and reliable so that the woman can participate in a normal life style without fear of embarrassing herself by accidentally voiding the contents of her bladder or constantly running to the bathroom to change pads. Still further, there is a need for medical personnel to conduct routine urinalysis on a clean urine sample so they can be aware of the onset of urinary infection or other medical events which can be identified by periodic urinalysis.

SUMMARY

The present invention is directed to a device and method that supplies these needs and eliminates the deficiencies of prior devices and systems.

The device of the invention comprises a valved drainage catheter for temporary placement in the female urethra. Additionally, the system also includes a sizing device for selecting the proper length catheter, a placement device to assure that the catheter is properly positioned and instruments to aid in opening the valve in the catheter.

The catheter comprises a hollow tube with an extendable mushroom head on the internal end, a mushroom shaped cap on the external end and a manually openable valve between the internal end and the external end or within the mushroom shaped cap on the external end to prevent urine from exiting the catheter prematurely. Also, the catheter includes one or more sensors to measure bladder pressure and chemical and physical properties of the urine, means to transmit information generated by the sensors to a remote location and, if necessary, energy sources to power the sensors and transmission device. The sizing device is of similar shape as the drainage catheter except the catheter has a longer length, the outer surface has measurement indicia spaced along its length and the mushroom cap is replaced by a removable disc shaped similar to the mushroom cap. After insertion of the sizing device in the urethra, the disc is slid along the external portion of the catheter until it rest snugly against the perineal area. The indicia exposed below the disc indicates the correct catheter length for a proper fit.

To place the catheter, the system includes a stylet for insertion into the catheter. Drainage is accomplished by using specially designed valve openers.

DRAWINGS

These and other features, aspects and advantages of the present invention will become better understood with reference to the following description, appended claims, and accompanying drawings, where:

FIG. 7 is an enlarged cutaway side view of the valve section of the drainage catheter of FIG. 2 with a drainage straw inserted.

FIG. 8 is an enlarged cutaway side view of the valve section of the drainage catheter of FIG. 2 showing an alternative construction with a plug inserted.

DESCRIPTION

Figures 1, 2:
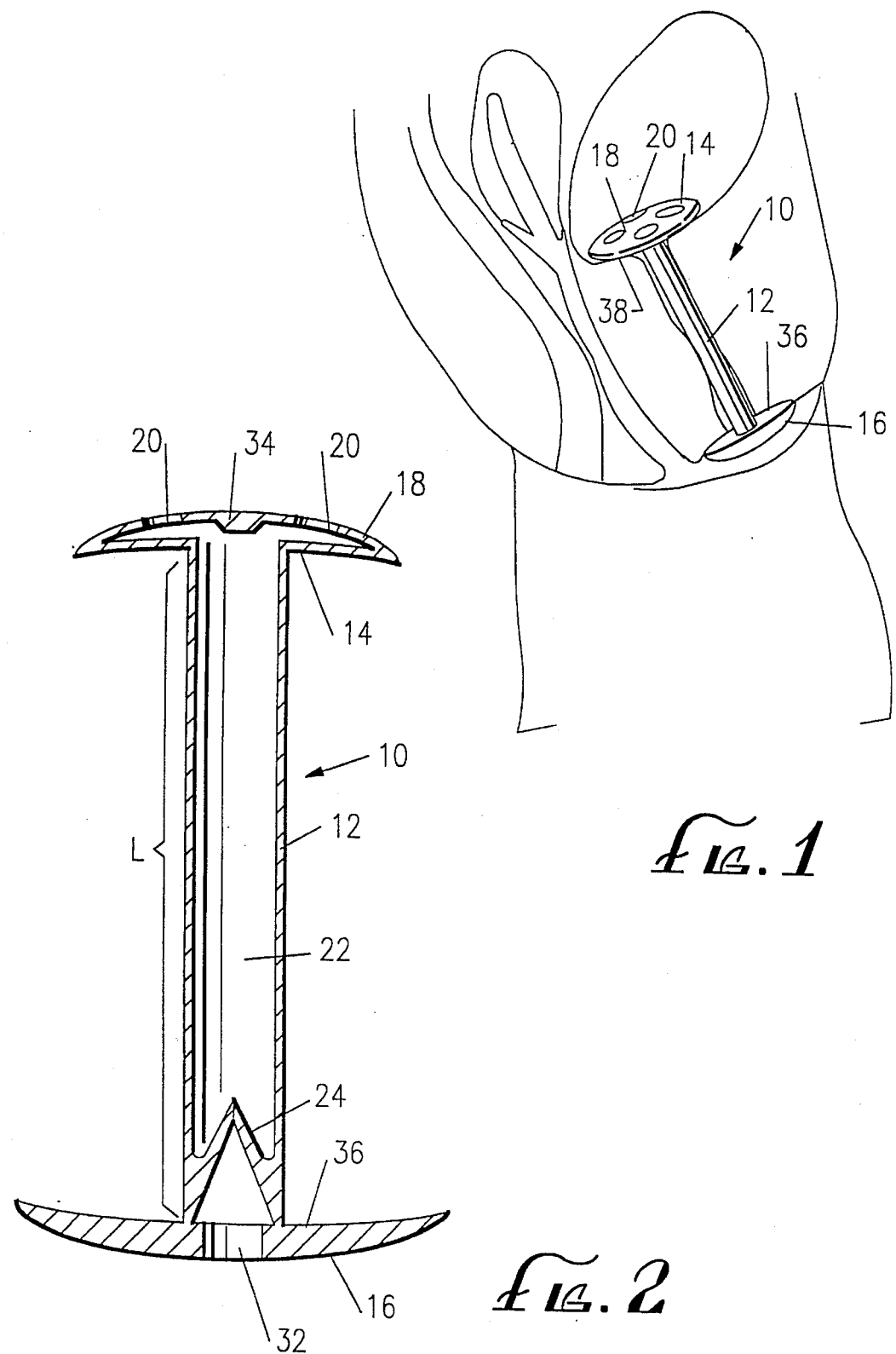
FIG. 1 is a side view showing the drainage catheter placed in the urethra of a female, the female body being shown in cross section.
FIG. 2 is a cutaway side view of the drainage catheter taken along line 2—2 of FIG. 1.

FIGS. 1 through 16 show drainage catheters embodying features of the invention.

The drainage catheter 10 includes a tubular center section 12 with a sealing portion on the internal end 14 and a cap 16 on the external end. In the embodiment shown in FIG. 2, the sealing portion is a mushroom shaped crown 18 which can be extended for placement of the catheter. The crown has several drainage holes 20 located in its upper surface. Enclosed in the lumen 22 of the catheter is a one way valve 24 which can be opened by the woman using the catheter 10. In the center of the cap is an drainage outlet 32.

Figure 3:
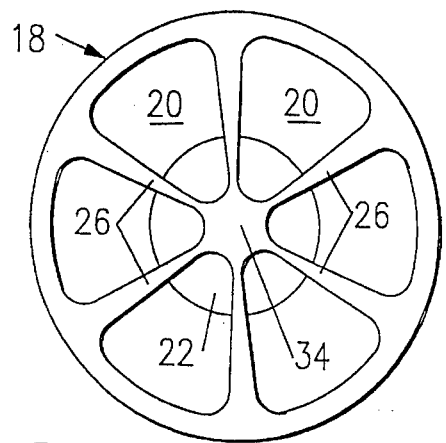
FIG. 3 is a top view of a first embodiment of the internal end of the drainage catheter of FIG. 2.
Figure 4:
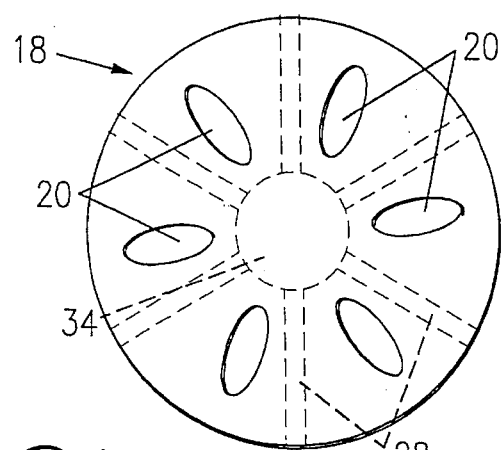
FIG. 4 is a top view of a second embodiment of the internal end of the drainage catheter of FIG. 2.

Alternate designs for the top surface of the crown 18 are shown in FIGS. 3 and 4. FIG. 3 shows six large drainage holes 20 separated by spokes 26. FIG. 4 shows a similar crown 18 design having smaller holes 20 in the crown surface 28. Shown in phantom in FIG. 4 are struts which depend from the lower or inner surface of the crown 18 to assure that drainage through the holes 20 and into the lumen 22 is not blocked.

Figure 5:
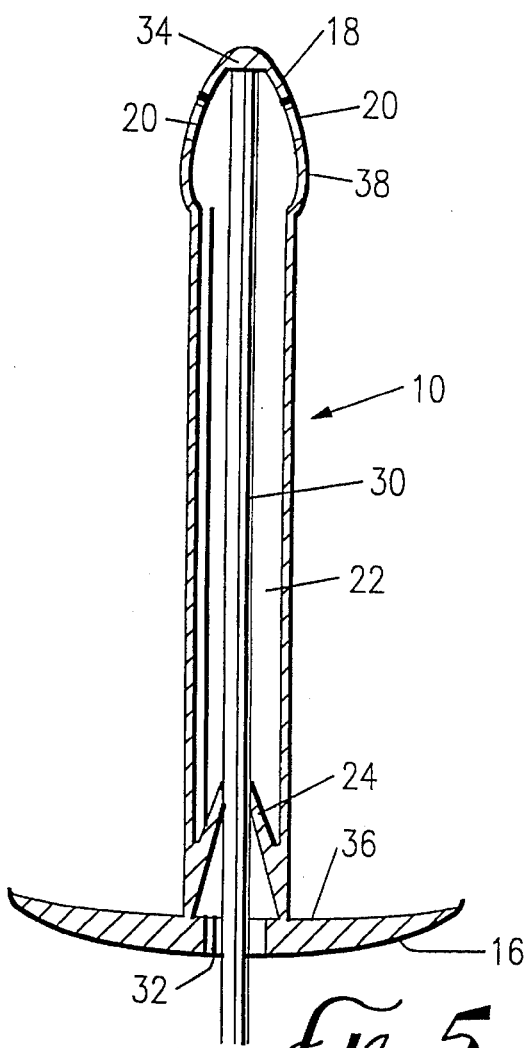
FIG. 5 is a cutaway side view of the drainage catheter taken along line 2—2 of FIG. 1, the catheter being extended for placement.
Figure 6:
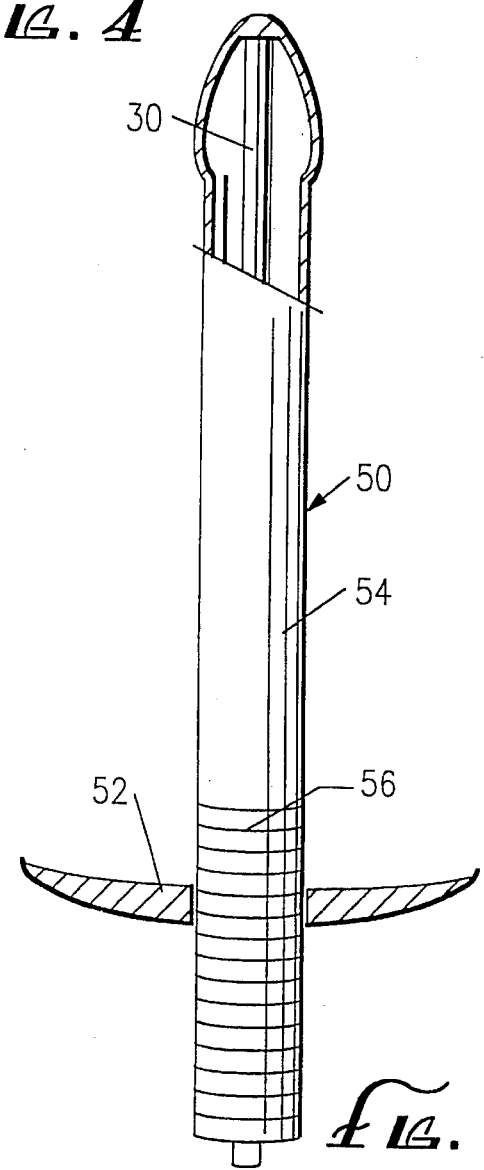
FIG. 6 is partial cutaway view of a sizing device.

The valve 24 shown in FIGS. 2, 5 and 7 is of a duck bill design which prevents fluid from descending down the tube unless the valve is purposefully opened. FIGS. 8–12 show two alternative valve structures and FIG. 14 incorporates a slit valve structure which will be discussed below.

To insert the catheter 10 into the female urethra a stylet 30 is inserted through the drainage outlet 32 and valve 24 until it comes in contact with the reinforced center 34 of the crown 18. The stylet 30 is then advanced further extending the crown 18 until the diameter of the outer surface of the crown is about the same as the diameter of the catheter 10. The extended crown 18 is then inserted through the external opening of the urethra and advanced until it enters the bladder. If the catheter is properly sized, the inner surface 36 of the cap 16 should be resting snugly against the skin surrounding the external opening of the urethra. Insertion of the catheter 10 may be assisted by applying a small amount of a sterile lubricant to the crown 18. The stylet 30 is then removed while the cap 16 is held in place. Removal of the stylet 30 allows the crown 18 to return to its normal shape with the crown inner surface 38 resting against the bladder surface as shown in FIG. 1.

In order to minimize or eliminate leakage around the catheter 10 the length L from the crown inner surface 38 to the cap inner surface 36 should be accurately determined. To do so the sizing device 50, shown in FIG. 5, is used. The sizer 50 is of substantially the same shape and has the same outer dimensions as the catheter 10 with the exception that the sizer is longer in length than the catheter 10. However, in place of the cap 16 the sizer 50 has a removable disk 52 which can slide along the outer surface of the sizer tube 54. At least a portion of the tube outer surface has indicia 56 thereon for use in selecting the proper catheter length L. Using the stylet 30 the sizer 50 is inserted into the urethra and the crown is allowed to prolapse against the bladder neck. The disc 52 is then slid along the sizer outer surface until it rests snugly against the tissue surrounding the urethra and the measurement marked on the outer surface of the tube 54 is read. The measurement indicates the catheter size to use for proper fit.

FIG. 7 shows the valve section of the catheter of FIG. 2 greatly enlarged to show the functioning of the valve during a drainage procedure. To drain the bladder a sterile spike 60 is inserted through the drainage outlet 32 in the external end of the implanted catheter 10. The spike 60 has a center portion 64 sized to fit snugly in the drainage outlet 32 and to open the valve 24. The spike 60 has a tapered head 62 on the top end of the tubular center portion 64 and an enlarged diameter handle 66 on the lower portion. Ports 72 are located at the juncture of the head 62 with the central portion 64. A central lumen 68 starts at the ports 72 and runs the length of the spike 60 terminating in an opening 70 at the base of the handle 66. While the diameter of the central portion 64 is sized to fit snugly through the drainage port 32, the handle diameter is chosen so that it will not easily enter the drainage port 32, thus preventing the head 62 of the spike from being inserted to far into the catheter 10 and damaging the crown 18 or the bladder. Additionally, the combined length of the head 62 and the central portion 64 is chosen so that when the top end 74 of the handle 66 rests against the drainage opening 32, the head 62 pierces the drainage outlet 32 and the valve 24, exposing the ports 70 to a standing column of urine in the catheter 10 above the valve 24. This cooperation of parts allows the user to drainage the bladder without soiling her hands from leaking urine. Once drainage is complete the spike is withdrawn and the valve closes and seals. The spike can then be disposed of or resterilized.

FIG. 8 shows and alternate valve mechanism comprising a plug 80 sized to fit in the drainage opening 32. The plug can be used in place of the valve 24 (as shown in FIG. 8) or in combination with the valve 24 as additional protection against leakage (not shown). The plug is shown with a draw string 82 and a pull tab 84.

Figure 9:
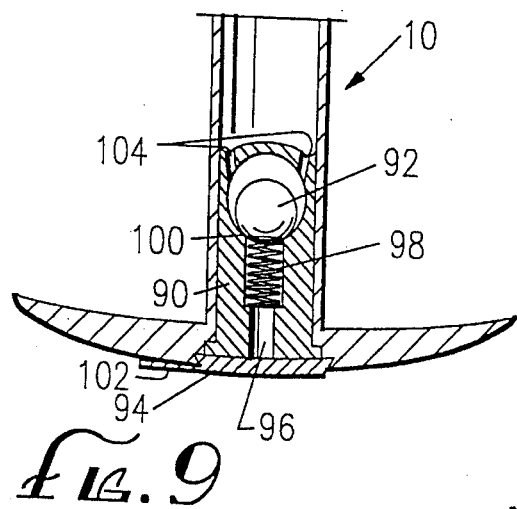
FIG. 9 is an enlarged cutaway side view of the valve section of the drainage catheter of FIG. 2 showing an alternative construction with a magnetic ball valve inserted, the valve being in its closed position.
Figure 10:
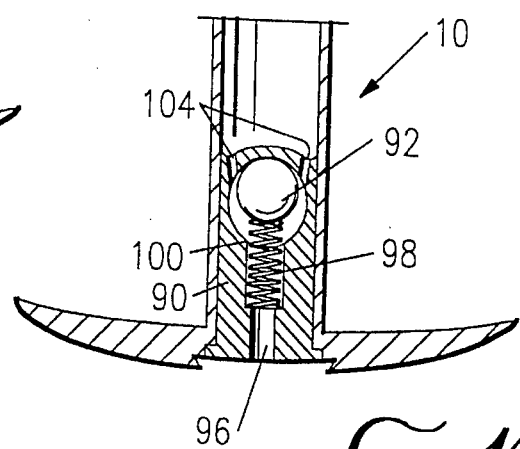
FIG. 10 is an enlarged cutaway side view of the alternative valve section of FIG. 9 in its open position.

FIGS. 9 and 10 show the catheter 10 with a ball valve mechanism 90 inserted in the external end of a drainage catheter 10. The catheter 10 is shown to have a uniform inner diameter along it entire length. After insertion of the catheter 10 using the stylet 30 and removal of the styler the ball valve 90 is placed and secured in the catheter 10. The ball valve 90 comprises a ball 92 which is attracted by a magnetic disc 94 placed over the drainage outlet 96. Also enclosed in the valve 90 is a spring 98 which lifts the ball 92 off the seat 100 when the magnetic disc 94 is removed. To raise the ball 92 off the seat 100 the tab 102 is grasped and pulled downward. The removal of the magnetic force allows the spring to lift the ball 92 unsealing the drainage outlet 96 so that the urine can flow through the valve openings 104 and out the catheter 10.

Figure 11:
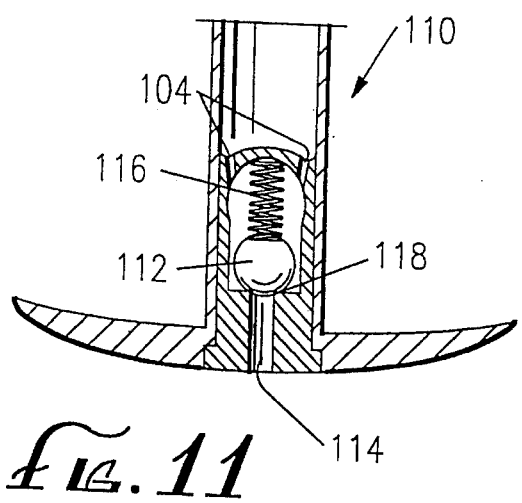
FIG. 11 is an enlarged cutaway view of the valve section of the drainage catheter of FIG. 2 showing a second alternative ball valve structure in its closed structure.
Figure 12:
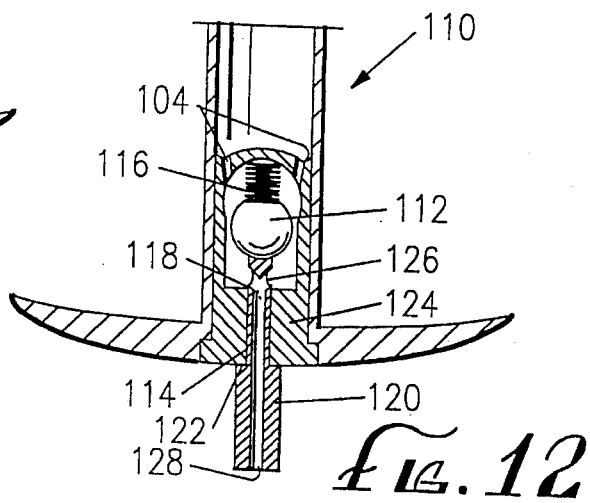
FIG. 12 is an enlarged cutaway side view of the second alternative valve section of FIG. 11 in its open position.

FIGS. 11 and 12 show the catheter 10 with a ball valve mechanism 110 inserted in the external end of a drainage catheter 10. Like the embodiment shown in FIGS. 9 and 10, the catheter is also shown to have a uniform inner diameter along its entire length. The valve mechanism 110 is inserted into the catheter 10 after its placement in the urethra. The ball valve 110 comprises a ball 112 which is held against the drainage opening 114 by the spring 116. To raise the ball 112 off the seat 118 a spike 120 is inserted through the drainage opening 114 until the shoulder 122 contacts the bottom 124 of the valve, compressing the spring 116 allowing urine to flow through the valve 110, ports 126 and drainage channel 128 through the center of the spike 120.

FIGS. 13 through 16 show the catheter 10 with a slit valve mechanism 140 inserted in cap 16 at the external end of a drainage catheter 10. Like the embodiments shown in FIGS. 1 through 12, the catheter 10 is also shown to have a uniform inner diameter along its entire length. The slit valve 140 includes a center portion 142 curved inward towards the catheter lumen 22 with a slit 144 located in the center thereof. The slit 144 is a one way valve which acts in the same manner as the duck bill valve discussed above in regard to FIGS. 1–7. To open the slit 144 a spike 120 is inserted through the slit 144 until the shoulder 122 contacts the center portion 142 of the valve allowing urine to flow through the ports 72, drainage channel 128 and through the center of the spike 60.

Figure 16:
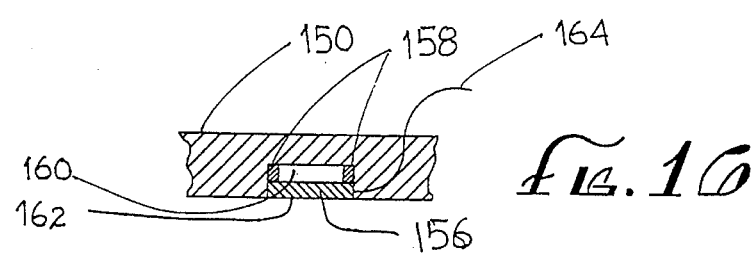
FIG. 16 is an enlarged cutaway side view of the pressure transducer mounted in the sensor ring portion of the second version of the drainage catheter taken along line 16—16 of FIG. 15.

To aid in holding the slit valve 140 in the cap 16, a locking ring 146 is positioned against the internal surface of the slit valve 140, locking the edge 148 of the slit valve 140 against the internal surface of the cap 16. Positioned internally of the locking ring 146 is a sensor ring 150 enlarged and shown in a cutaway view in FIG. 15. As the bladder fills with urine the area within the catheter 10, including the lumen 22 and volume 152 enclosed by the cap 16, also fills with urine and the pressure within the bladder is uniformly distributed throughout the volume of urine. Mounted in the sensor ring 150 is a pressure sensor 154 such as a pressure transducer or piezoelectric chip 156. An example of a pressure sensor using a piezoelectric chip is shown in FIG. 16 wherein in the chip 156 is mounted between two edge supports 158 over an enclosed air space 160. Pressure against the face 162 of the chip causes the chip 156 to bend into the air space and, in turn, create an electrical signal which can be detected, measured, and correlated with the pressure applied to the face 162. The signal transmitted along electrical lead 164 can then be fed directly to a monitoring device or to a signal transmitter 166, such as an FM transmitter, for monitoring at a remote location. The transmitter can be powered by a power source 168 also mounted in the sensor ring 150 or external of the catheter. In a still further embodiment, the sensor ring may include positive and negative electrodes 170, 172 composed of dissimilar metals. The normal urine is usually acidic with a pH of 5.5–6.5 and thus can act as a conductive medium which can serve as the electrolyte creating a battery in conjunction with the positive and negative electrodes 170, 172. Abnormal urine may have a pH from 5 to 8.5. The assembly creates an electrical current which can be stored in the power source 168 or directly power the transmitter 166.

Figure 13:
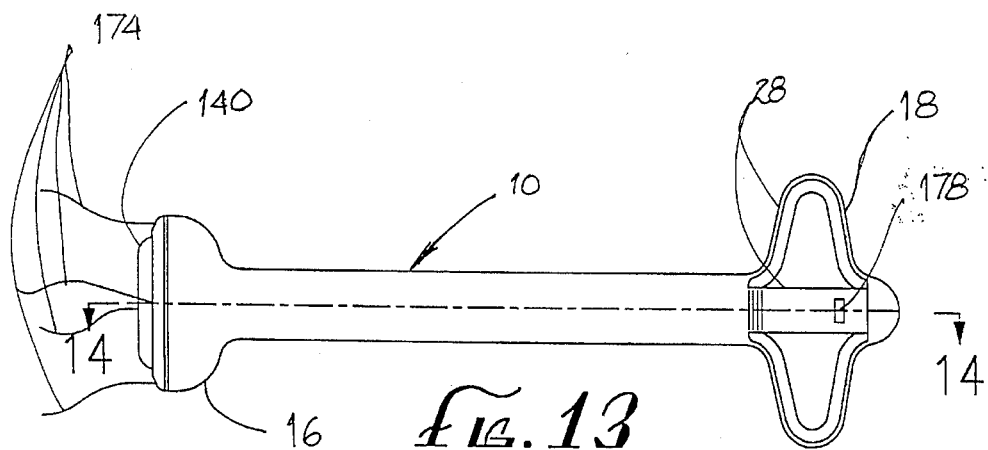
FIG. 13 is a side view of a second version of a drainage catheter for controlling female incontinence.
Figure 14:
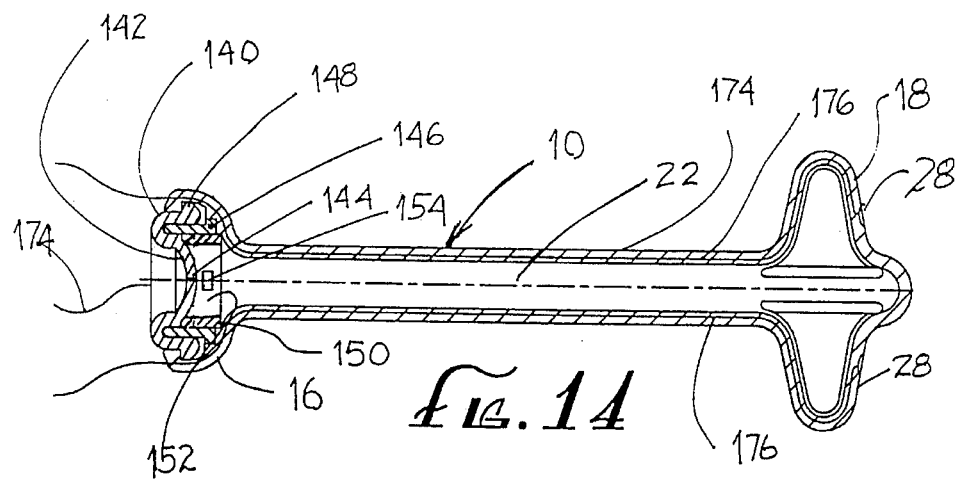
FIG. 14 is a cutaway side view of the second version of the drainage catheter taken along line 14—14 of FIG. 13.
Figure 15:
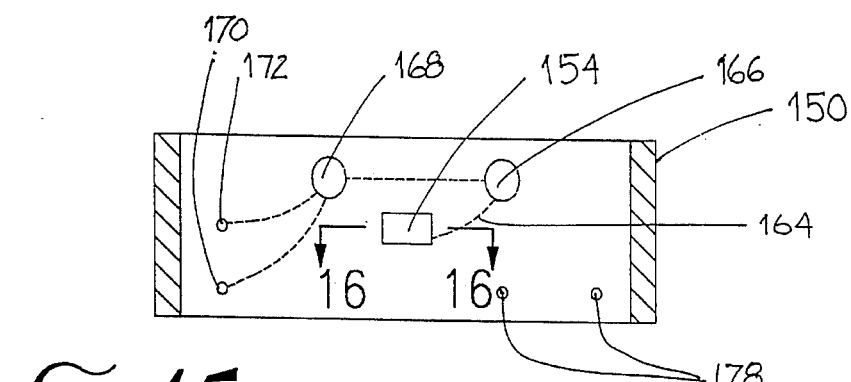
FIG. 15 is an enlarged cutaway side view of the sensor ring portion of the second version of the drainage catheter taken along line 14—14 of FIG. 13.

Imbedded in the wall 174 and extending along the length of the catheter 10 are signal transmission means 176, such as electrical wires or optical fibers, which are connected on a first end to sensors 178 and on a second to a signal receiver (not shown). The sensors are located in the crown 18 with their sensing surfaces being exposed to the urine in the bladder. The sensors 178 can have various different capabilities which one skilled in the art of urinalysis would recognize and find valuable in monitoring a patient. For example, the sensors 178 can electrically or optically detect pH, temperature, pressure and various different chemical constituents of urine such as sodium, potassium, glucose, drug markers and metabolites, specific gravity, proteins, leukocyte esterase, nitrites, urobilinogen, whole or crenated blood cells, ketones, bilirubin, turbidity and color. FIGS. 13 and 14 show a crown 18 with four struts 28 and four sensors. However, this is not intended to place a limit on the number of sensors as more than one signal transmission means can be placed along a strut 18, more than four struts 18 can be used, as shown in FIGS. 3 and 4, or a single sensor can detect various different materials. As an example, an optical fiber capable of transmitting IR or UV light can be used.

Different frequency light transmitted along the signal transmission means can directly, or as a result of signal responsive fluorescence, quantitatively or qualitatively determine chemical constituents in the urine in the bladder.

While FIG. 14 shows the signal transmission means 176 exiting through the cap 16, it is also contemplated that they can be connected directly to the sensor ring 150 and the signal transmitted as described above. As a further alternative, the sensors 178 can be mounted directly on the sensor ring 150. This presents a particular advantage for optical sensing as transmitter and receiver fiber ends can be mounted opposite each other to detect and analyze light transmitted through the urine.

A particular advantage of the embodiment incorporating sensors and a signal collection and/or transmission means is that nursing personnel can readily monitor a bedridden patient or a patient unable to manipulate the drainage device. Pressure signals from the pressure sensor 154 will indicate when the patient has to void so that assistance can be provided before the bedlinens are soiled. Abnormal temperature readings can be indications of and early warnings of bladder or systemic infection so that treatment can be instituted at an early stage. The online, continuous chemical analysis of the urine can be a valuable addition to control of drug treatment or a diagnostic tone in the indication of the need for additional or changed treatment.

Figure 17:
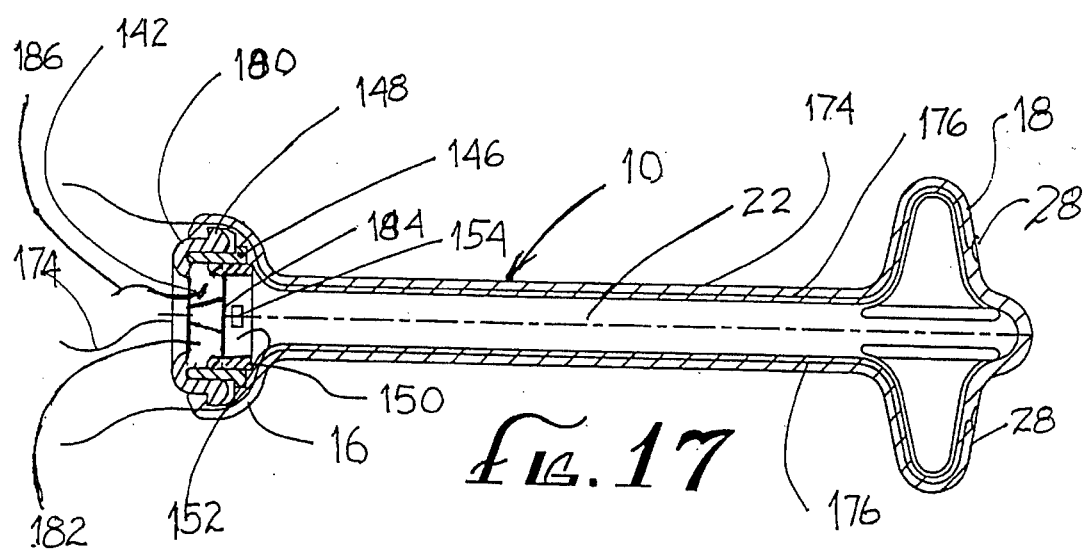
FIG. 17 is a cutaway side view of the second version of the drainage catheter taken along line 14—14 of FIG. 13 showing a further valve design.

A still further version of the urinary drainage catheter, shown in FIG. 17, includes an electrically activated valve 180. The valve, which comprises a valve body 182 and a movable plug 184, can be opened by an electrical signal transmitted along an input lead 186 or by way of a radio signal (i.e., a short range FM signal) transmitted to a receiver (not shown) in the valve 180 or in the sensor ring 150, the receiver being operatively connected to the movable plug 184.

The catheter 18 can be fabricated from a broad range of materials presently used for forming urinary catheter including, but not limited to natural and synthetic rubbers, silicone rubbers, thermoplastic elastomers, latex, polyvinyl chloride, polyethylene, and PTFE with or without coatings such as silicone materials, Teflon, hydrophilic compounds and other materials which improve the compatibility with mucosal tissue. Additionally, antibacterials, anti-inflammatory drugs, antibiotics or other drugs can be coated on the catheter surface or absorbed into the coatings on the catheter surface. In the embodiment of FIGS. 9 and 10, the ball 92 is a magnetic material, preferentially a plastic material having magnetic materials or magnetizable materials dispersed therein or ceramometallic materials. The spike 66 or 120 may be formed from a broad range of materials. Stiffness during use is the primary design criteria. Secondly, since the spike is intended to be disposable, the material should be inexpensive. While materials like polyethylene or polypropylene are suitable, a particularly preferred material is a material slowly dissolvable in water or biodegradable so that the spike can be disposed of into the toilet without clogging the plumbing system. The sensors, signal transmission means, power source and other components of the embodiment of FIGS. 13–16 can be selected from a broad range of components commonly used for these purposes.

The dimensions of the catheter are dependent on the dimensions of the anatomy of the patient into which the catheter is being placed. The outer diameter of the tubular section 12 of the catheter is about 8 mm and the effective length between the cap 16 and the crown 18 is between about 2.5 and 4.5 cm. However, as indicated, the dimensions can be selected to create a non-leak seal with the patients urinary tract. The diameter of the cap and the crown is from about 12 to 17 mm.

The present invention has been described in considerable detail with reference to certain preferred versions and uses thereof, other versions and uses are possible. Other valve designs, dimensions, materials or crown designs may be used without changing the inventive concept. Additionally the sensor capability described for one particular embodiment of the valved catheter can be incorporated in the other versions shown herein or in prior art indwelling urinary catheters. Therefore, the scope of the appended claims should not be limited to the description of the preferred versions contained herein.

What is claimed is:

1. A urinary drainage catheter for placement in the female urethra, the urethra having an exterior opening at the point of exit from the body and an interior opening at the point of entry into the urinary bladder, the catheter comprising a hollow shaft, a sealing portion on a first end of the shaft and a cap on a second end of the shaft, and sensors mounted therein, wherein:

the hollow shaft has a length sized to approximate the length of the urethra and an outer diameter approximating the diameter of the urethra such that the shaft does not extend beyond the opening of the urethra, the sealing portion having
 a) an upper surface with openings therein so that fluid in the bladder can enter the shaft, and
 b) a width greater than the outer diameter of the shaft, the width of the sealing portion being reducible so that the sealing portion can be readily passed through the urethra, a lower surface of said sealing portion resting against the interior end of the urethra, and the cap having a width greater than the outer diameter of the shaft, an upper surface of said cap resting against the exterior opening of the urethra, no portion of the urinary drainage catheter extending exterior of the urethra past the cap, said sensors having the capability to detect properties of urine in the bladder, the sensors being connected to transmission means for delivering signals representative of the properties detected by the sensors.

2. The urinary drainage catheter of claim 1 further including a valve within the cap to control flow of fluid through the catheter and a pressure sensor mounted in a space enclosed by the cap and located between the valve and the hollow shaft.

3. The urinary drainage catheter of claim 2 wherein the valve is operated by an electronic signal delivered from a transmitter located remotely from the catheter.

4. The urinary drainage catheter of claim 2 further including sensors to detect or measure physical and chemical properties of the urine within the bladder.

5. The urinary drainage catheter of claim 4 wherein the sensors are selected from the group consisting of devices capable of qualitatively or quantitatively sensing pressure, pH, temperature, various different chemical constituents of urine, sodium, potassium, glucose, drug markers, drug metabolites, specific gravity, proteins, leukocyte esterase, nitrites, urobilinogen, whole or crenated blood cells, ketones, bilirubin, turbidity and color.

6. A urinary drainage control and bladder monitoring system comprising a valved urinary drainage catheter for placement in the female urethra, the urethra having an exterior opening at the point of exit from the body and an interior opening at the point of entry into the urinary bladder, a stylet for use in placing the catheter, a hollow spike for opening the valve to allow drainage of fluid from the bladder and sensors to monitor physical and chemical properties of urine, the catheter comprising a hollow shaft with a lumen longitudinally through its center, a sealing portion on a first end of the shaft, a cap on a second end of the shaft, no portion of the urinary drainage catheter extending exterior of the urethra beyond the cap, a valve located within the catheter, and sensors mounted on the catheter in contact with urine to be drained through the catheter, wherein:

the shaft has a length sized to approximate the length of the urethra and an outer diameter approximating the diameter of the urethra such that the second end of the shaft is located at the exterior opening of the urethra, the sealing portion has a width greater than the outer diameter of the shaft, there being openings through the sealing portion so that fluid in the bladder can enter the shaft lumen, the width of the sealing portion being reducible so that the sealing portion can be readily passed through the urethra, the cap has a valve therein in line with the lumen through the shaft and a width greater than the outer diameter of the shaft, the stylet is a stiff rod with a diameter less than the inner diameter of the shaft and a length greater than the length of the catheter such that insertion of the stylet through the lumen of the catheter and pushing the stylet against the sealing portion causes the sealing portion to elongate and the width to reduce to a diameter suitable for passing through the urethra, the spike having an insertion portion, an exterior portion, a flange on an outer surface thereof separating the insertion portion from the exterior portion, a diameter approximating the inner diameter of the shaft and a length sufficient to enter the valve, the exterior portion of the spike being sized for grasping in the fingers of a user such that when the insertion portion is passed through the valve in the cap and the flange is in contact with the cap the valve opens allowing fluid to drain from the bladder through the shaft, valve and the lumen of the spike without soiling the fingers of the user.

7. The urinary drainage control and bladder monitoring system of claim 6 wherein the sensors are selected from the group consisting of devices capable of qualitatively or quantitatively sensing pressure, pH, temperature, various different chemical constituents of urine, sodium, potassium, glucose, drug markers, drug metabolites, specific gravity, proteins, leukocyte esterase, nitrites, urobilinogen, whole or crenated blood cells, ketones, bilirubin, turbidity and color.

8. The urinary drainage control and bladder monitoring system of claim 6 further including a signal transmitter and signal transmission means connecting the sensors with the signal transmitter, the signal transmitter capable of delivering information obtained by the sensors to a remote location.

9. The urinary drainage control and bladder monitoring system of claim 8 further including a power source for supplying energy to the signal transmitter.

10. The urinary drainage control and bladder monitoring system of claim 9 wherein the power source comprises a positive and negative electrode located within a space enclosed by the catheter, the positive and negative electrode in contact with the urine, the urine being an electrolyte, the positive electrode, negative electrode and urine comprising a battery.

11. The process of monitoring chemical and physical properties of urine within the bladder of a female comprising:

determining the diameter and length of the female urethra and placing a catheter in the urethra, the catheter comprising:

a hollow shaft of an outer diameter approximating the diameter of the urethra, the shaft having a sealing portion on a first end and a cap on a second end, the distance between a lower surface of the sealing portion and an upper surface of the cap approximating the measured length of the urethra, a valve portion located between the sealing portion and the cap, and sensors mounted on the catheter in contact with urine within the bladder, the placement procedure comprising:

inserting a styler through the cap and valve along the length of a lumen in the shaft into contact with an inner surface on the sealing portion, further inserting the styler along the length of the lumen causing the inner surface of the sealing portion to be temporarily distended from the juncture of the sealing portion with the shaft and temporarily reducing the outer diameter of the sealing portion to a diameter approximating the diameter of the urethra, inserting the distended sealing portion followed by the shaft into the external opening of the urethra and along the length of the urethra until the sealing portion is in the bladder and the cap rests against the exterior opening of the urethra, removing the styler from the catheter allowing the sealing portion to resume its original configuration, and monitoring the signals generated by the sensors in contact with the urine.

12. The process of claim 11 wherein the sensors are selected from the group consisting of devices capable of qualitatively or quantitatively sensing pressure, pH, temperature, various different chemical constituents of urine, sodium, potassium, glucose, drug markers, drug metabolites, specific gravity, proteins, leukocyte esterase, nitrites, urobilinogen, whole or crenated blood cells, ketones, bilirubin, turbidity and color.

* * * * *